United States Patent
Feeman

[11] 3,971,769
[45] July 27, 1976

[54] SULFOALKYL AMINOPHENYL DISAZO DYES

[75] Inventor: James F. Feeman, Wyomissing, Pa.

[73] Assignee: Crompton & Knowles Corporation, New York, N.Y.

[22] Filed: July 5, 1973

[21] Appl. No.: 376,606

Related U.S. Application Data

[63] Continuation-in-part of Ser. No. 4,096, Jan. 17, 1970, abandoned, Continuation-in-part of Ser. No. 102,231, Dec. 28, 1970, abandoned.

[52] U.S. Cl............................... 260/186; 260/174; 260/177; 260/178; 260/184; 260/191; 260/196; 260/205; 260/206; 260/207; 260/207.1; 260/507 R; 260/508; 260/509

[51] Int. Cl.²..................... C09B 31/18; D06P 3/24; D06P 3/40; C09B 31/02

[58] Field of Search........... 360/184, 174, 177, 178, 360/186, 187, 191

[56] References Cited
UNITED STATES PATENTS

| | | |
|---|---|---|
| 2,045,323 | 6/1936 | Felix et al. .................. 260/186 X |
| 2,092,076 | 9/1937 | Knight ............................. 260/186 |
| 2,216,446 | 10/1940 | McNally et al. ............... 260/186 X |
| 2,221,029 | 11/1940 | McNally et al. ................. 260/206 |
| 3,709,870 | 1/1973 | Wolfrum........................... 260/186 |

Primary Examiner—Floyd D. Higel
Attorney, Agent, or Firm—William H. Elliott, Jr.

[57] ABSTRACT

Compounds useful as light fast yellow, orange and red dyes for natural and synthetic polyamide fibers and for secondary cellulose acetate fibers, have the structure:

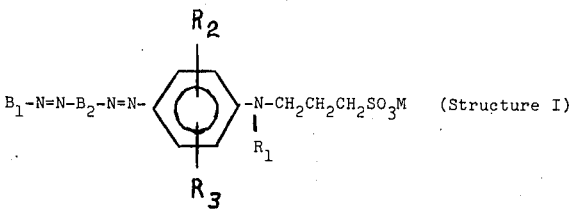

(Structure I)

wherein $R_1$ is alkyl, benzyl, cyclohexyl, —C—CH₂CH₂OH,

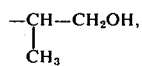

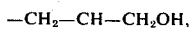

—CH₂CH₂CN, —CH₂CH₂—O—COCH₃, or

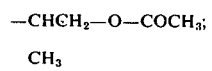

$R_2$ is —H, -alkyl, halogen, —O— alkyl or —NH—COR₄;

$R_4$, as used in $R_2$, $R_3$, $R_5$ and $R_6$, represents -alkyl, -tolyl, -phenyl or -halophenyl; and $B_1$ is a benzene ring or a benzene ring substituted with substituents which may be selected from nitro, halogen, cyano, alkyl, alkoxy, trifluoromethyl, alkylsulfonyl, acetyl, carboxamido, sulfonamido, N-alkyl-sulfonamido, N,N-dialkylsulfonamido, N-alkylcarboxamido and carboxyl groups;

$B_2$ is a 1,4-naphthylene or a 1,4-phenylene group of the structure:

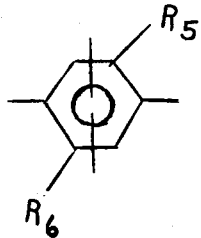

wherein
$R_5$ is —H, alkyl, -alkoxy, or —NHCOR₄;
$R_6$ represents —H, alkyl, alkoxy, —NHCOR₄, —NH—SO₂—R₄ or halogen; and
M is —H, —Na, —K, —Li or —NH₄.

3 Claims, No Drawings

SULFOALKYL AMINOPHENYL DISAZO DYES

This application is a continuation-in-part of application Ser. No. 4,096 filed Jan. 17, 1970 and application Ser. No. 102,231 filed Dec. 28, 1970; both of said applications are now abandoned.

This invention relates to water-soluble sulfoalkyl disazo acid dyes for natural and synthetic polyamide fibers and for secondary cellulose acetate fibers and to a method of making the dyes and to their utilization.

The new compounds of this invention have the structure:

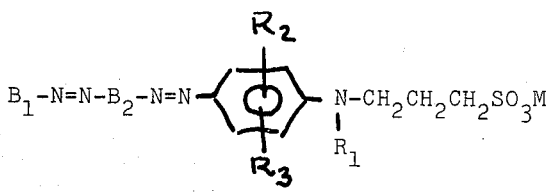

(Structure I)

wherein
  $R_1$ is an alkyl radical having from 1 to 8 carbon atoms, benzyl, cyclohexyl, —CH$_2$CH$_2$OH,

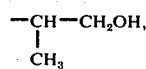

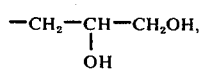

—CH$_2$CH$_2$CN, —CH$_2$CH$_2$—O—COCH$_3$, or

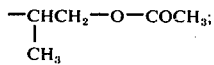

$R_2$ is —H, -alkyl having 1 to 4 carbon atoms, halogen, —O— alkyl having 1 to 4 carbon atoms or —NHCOR$_4$;
  $R_3$ represents —H, -alkyl having 1 to 4 carbon atoms, —O— alkyl having 1 to 4 carbon atoms or —NH—COR$_4$;
  $R_4$, as used in $R_2$, $R_3$, $R_5$ and $R_6$, represents -alkyl having 1 to 4 carbon atoms, -tolyl, -phenyl or -halophenyl; and
  $B_1$ is a benzene ring or a benzene ring substituted with substituents which may be selected from nitro, halogen, cyano, lower alkyl, lower alkoxy, trifluoromethyl, alkylsulfonyl, acetyl, carboxamido, sulfonamido, N-alkyl-sulfonamido, N,N-dialkyl-sulfonamido, N-alkylcarboxamido and carboxyl groups;
  $B_2$ is a 1,4-naphthylene or a 1,4-phenylene group of the structure

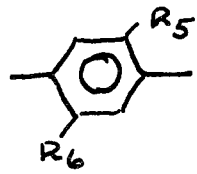

wherein
  $R_5$ is —H, -alkyl, -alkoxy, or —NHCOR$_4$;
  $R_6$ represents —H, alkyl, alkoxy, —NHCOR$_4$, —NH—SO$_2$—R$_4$ or halogen; and
  M is —H, —Na, —K, —Li or —NH$_4$.

These compounds are in general water-soluble acid dyes having a wide range of shades and exhibit good exhaustion from neutral to alkaline baths onto polyamides or secondary cellulose acetate rayon.

The Structure I compounds of this invention are made by diazotizing a 4-aminomonazo intermediate compound and coupling the diazonium salt with an intermediate of Structure II (below) in an aqueous solution, preferably at pH 2–7, and optionally converting the resulting reaction product to a desired salt form by appropriate acidification and/or neutralization.

The Structure II intermediates useful in producing the compounds of this invention have the structure:

wherein $R_1$, $R_2$, $R_3$ and M have the same meaning as in Structure I; such intermediates can be produced by methods known in the art — see Belgian Pat. No. 761,714. For reasons of economy a preferred subgroup of very useful intermediates include:
  N-ethyl-N-(m-tolyl)-3-amino-propane sulfonic acid
  N-methyl-N-(m-tolyl)-3-amino-propane sulfonic acid
  N-ethyl-N-phenyl-3-amino-propane sulfonic acid
  N-methyl-N-phenyl-3-amino-propane sulfonic acid
  and the various K, Na, Li, and NH$_4$ salts thereof.

Suitable 4-aminomonazo intermediate compounds useful in preparing the Structure I compounds of this invention include the 4-aminomonazo compounds made by coupling any of various anilines such as aniline, toluidines, anisidines, xylidines, phenetidines, 2-chloro-4-nitroaniline, nitroanilines, cyanoanilines, chlorocyanoanilines, nitrocyanoanilines, 2,6-dichloro-4-nitroaniline, 4-aminomethylsulfone, 4-aminoacetophenone, 2-amino-5-nitro-toluene, 2-amino-5-nitroanisole, 3-nitro-4-amino-toluene, 2,4- dichloroaniline, 2,5-dichloroaniline, 2-trifluoromethylaniline, 2-trifluoromethyl-4-chloroaniline, 2,4-dinitro-6-bromoaniline, 2-cyano-4,6-dinitroaniline, nitrocresidine, 2-amino-5-nitrobenzoic acid methyl ester, 3-nitro-4-aminobenzoic acid butyl ester, 4-aminobenzoic acid methyl ester, 4-aminoacetanilide, 3-aminobenzanilide, 4-aminobenzene sulfonamide, N',N'-dimethyl-4-aminobenzene sulfonamide, etc., with 1-naphthylamine, aniline or any of various aniline derivatives which are unsubstituted para to the -NH₂ group including o-toluidine, m-toluidine, o-anisidine, m-anisidine, o-phenetidine, cresidine, 2,5-dimethoxyaniline, 2,5-diethoxyaniline, m-aminoacetanilide, 4-acetylamino-2-aminotoluene, monobenzoyl-m-phenylene diamine, 2-amino-4-acetylaminoanisole, 2-amino-4-acetylamino-phenetole, m-chloroaniline, m-bromoaniline, or monomethanesulfonyl-m-phenylene diamine. The preceding anilines are all known compounds.

Until now there has been a definite need for acid dyes having good solubility in water which could be applied to secondary cellulose acetate fibers to produce dyeings having good lightfastness and wetfastness. Conventional water-insoluble dispersed dyes which are in general use for dyeing cellulose acetate are notoriously lacking in fastness to washing and other wet treatments. Many previously available acid dyes which dye cellulose acetate from salt baths are deficient in other respects. They lack affinity for the fiber, have poor lightfastness or are uneconomical because of high cost of manufacture or low tinctorial value.

The present invention, however, particularly those dyeing in yellow, orange or red shades, overcome the deficiencies listed above, in that they are economical to manufacture, dye acetate rayon in bright, light to heavy depths of shade, have very good lightfastness, have good to excellent wetfastness properties and have outstanding solubility in water.

In addition these dyes have been found commercially useful for dyeing and printing nylon fabrics to produce level, lightfast yellow, orange and red shades. Their exceptionally good water solubility combined with good lightfastness, neutral-alkaline affinity and level dyeing properties allow them to fill needs in the textile dyeing industry.

This unusual combination of properties, in particular the high water-solubility plus good neutral-alkaline affinity and "pile-on" to heavy depths of shade, exhibited by many of the compounds of this invention, allows their use in applications where short dye:liquor ratios are required such as in jig and pad dyeing and in printing operations.

A preferred subgroup of Structure I compounds of the invention have the structure:

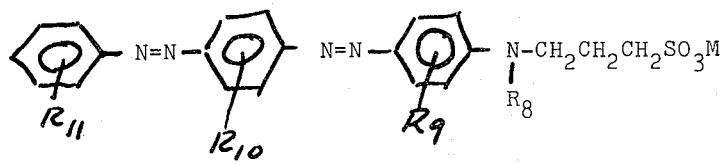

wherein
$R_8$ is alkyl having 1 to 8 carbon atoms, $-CH_2CH_2CN$, $-CH_2CH_2OH$, cyclohexyl, or benzyl;
$R_9$ is $-H$ or $-CH_3$
$R_{10}$ is $-H$ or $-CH_3$ and
$R_{11}$ is $-H$ or $-CH_3$ The disazo dyes of this preferred subgroup may be prepared by diazotizing 4-aminoazobenzene, 4-aminoazotoluene or a 4-amino-methylazo-benzene and coupling with a Structure II intermediate in which $R_1$ is an alkyl radical having 1 to 8 carbon atoms, $-CH_2CH_2CN$, $-CH_2CH_2OH$, cyclohexyl, or benzyl.

This preferred subgroup includes yellow to red acid dyes some of which have outstanding fastness to light, good fastness to washing, excellent solubility in water, excellent substantivity for cellulose acetate rayon and nylon and may be produced economically from commercially available intermediates.

The compounds of this invention are usually formed as sodium salts of the sulfonic acid and they can be used as such or converted to the free sulfonic acid by treatment with an inorganic acid and the free acids can then be converted to various other salts such as $-Na$, $-K$, $-Li$ or $-NH_4$ by neutralization with a suitable hydroxide, carbonate or ammonia.

Although in the list of suitable anilines the chloro derivatives are sometimes specified, there is no technical reason for not believing that other correspondingly structured halo derivatives, namely the $-Br$, $-F$ and $-I$ derivatives, (when available) would be operable and substitutable for the chloro derivatives specified. Similarly in the Structure I definitions of $R_1$, $R_2$, $R_3$, $R_4$, $R_5$ and $R_6$ where the term halogen or halo is used, the intermediates for producing the chloro derivatives are usually the most readily available and cheapest, however there is no technical reason for not believing that other correspondingly halo derivatives, namely the $-Br$, $-F$, and $-I$ derivatives (when available) would be operable for the purposes of this invention.

Throughout the application (unless otherwise specified) where the term alkyl is used, it is intended to indicate an alkyl chain of any length that will not adversely influence the solubility of the dye, and particularly the lower alkyls having 1 to 5 carbons.

The following examples will serve to illustrate the preparation of representative dyes of this invention, the utilization of the dyes in the dyeing of polyamides and secondary cellulose acetate fibers, and the novel dyeings thereby produced.

In these examples, parts and percentages are by weight and temperatures are in degrees centigrade, unless otherwise stated.

EXAMPLE 1

4-Aminoazobenzene hydrochloride (23.3 parts) was slurried in 125 parts of water and 15 parts of 32% hydrochloric acid. After stirring one hour the mixture was diluted with ice and water to 375 parts by volume at 12°. A solution of 8.3 parts of sodium nitrite in 25 parts of water was added during 45 minutes at 12°. The mixture was stirred one hour longer at 12°–16° and ice added to 19°. The solution was treated with 1 part of filteraid and filtered to remove a small amount of insoluble matter. The resultant diazonium salt solution, after decomposition of a small excess of nitrous acid by addition of sulfamic acid, was run with good stirring into 185 parts of N-ethyl-N(m-tolyl)-3-amino-propane sulfonic acid (sodium salt) in which had been dissolved 25 parts of sodium acetate and which had been cooled to 5° with ice. After 45 minutes the pH was raised to 5 by addition of 20% sodium hydroxide solution, and after 2 hours more to pH 8.7 with additional sodium hydroxide. The red crystalline product was then filtered and dried giving a reddish-brown solid having the structure:

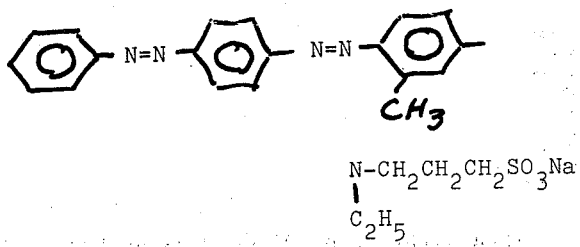

This compound dyed nylon and other polyamide fibers from alkaline, neutral, and weakly acid aqueous baths in level red shades having very good fastness to light and washing. It also dyed secondary cellulose acetate fibers from aqueous baths containing 20% o.w.f. of sodium chloride in red shades having excellent fastness to washing and good fastness to light.

Using the general procedures of Example 1, further Structure I disazo acid dyes having similar dyeing and fastness properties were obtained by diazotizing 4-aminoazobenzene or 4-aminoazotoluene and coupling with an intermediate having the structure:

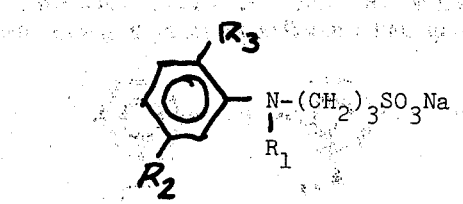

are listed in Table I.

The diazo solution was filtered after 30 minutes and a slight excess of nitrous acid decomposed with sulfamic acid. To this solution was added a solution of 7 parts of cresidine in 50 parts of water and 6 parts of hydrochloric acid. After stirring 18 hours coupling was nearly complete. The aminomonoazo intermediate was filtered, repasted in 250 parts of water and 15 parts of concentrated hydrochloric acid and diazotized at 25° by adding a solution of 3.7 parts of sodium nitrite. The diazonium salt crystallized out as a golden solid which was filtered after 30 minutes. The paste was dissolved in 500 parts of water at 25° C. and, after filtration, added to a solution of 16 parts of the K salt of N-ethyl-N-(m-tolyl)-3-aminopropane sulfonic acid in 50 parts of water and 5 parts of sodium acetate, and the solution iced to 0°C. Coupling was rapid giving a dark colored solid precipitate which was made alkaline with 50% sodium hydroxide, filtered and dried. It had limited water solubility but dyed nylon from alkaline baths in dull violet shades.

EXAMPLES 15 – 23

2-Chloro-4-nitroaniline (34.6 parts) was pasted in 200 parts of water and 60 parts of concentrated hydrochloric acid and diazotized directly at 10°–15° C. by addition of 16 parts of sodium nitrite as an aqueous solution. After 1 hour the diazo solution was filtered and excess nitrous acid decomposed with sulfamic acid. To the clear solution, iced to 0°, was added 30.6 parts of 2,5-dimethoxyaniline dissolved in 50 parts of water and 25 parts of concentrated hydrochloric acid. The mixture was stirred at 10°–15° for 15 minutes after which coupling was complete. Then during 10 minutes was added at 15°–20° a solution of 16 parts of sodium nitrite and 40 parts of concentrated hydrochloric acid. The aminoazo intermediate dissolved upon diazotization. After stirring about 1 hour the diazonium salt crystallized out and was filtered. The paste was redissolved in 500 parts of water as an orange-red solution, filtered to remove some unrediazotized material and divided into eight equal amounts of solution, and a portion added to each of the couplers listed in Table II below which were used in 0.03 molar amount, dissolved in 50 parts of water and 5 parts of sodium ace-

TABLE I

| Example No. | Aminoazo Compound Diazotized | Intermediate Substituents | | | Shades of dyeings on nylon or acetate |
|---|---|---|---|---|---|
| | | $R_1$ | $R_2$ | $R_3$ | |
| 2 | 4-Aminoazobenzene | —CH$_3$ | H | H | scarlet |
| 3 | 4-Aminoazotoluene | —CH$_3$ | H | H | scarlet |
| 4 | 4-Aminoazobenzene | —CH—CH$_2$CH$_3$ | H | H | scarlet |
| | | CH$_3$ | | | |
| 5 | 4-Aminoazobenzene | —Cyclohexyl | H | H | scarlet |
| 6 | 4-Aminoazobenzene | —CH$_2$CH$_2$OH | H | H | scarlet |
| 7 | 4-Aminoazobenzene | —CH$_2$CH$_3$ | H | —CH$_3$ | scarlet |
| 8 | 4-Aminoazotoluene | —CH$_2$CH$_3$ | —CH$_3$ | H | red |
| 9 | 4-Aminoazobenzene | —CH$_2$CH$_2$CN | —CH$_3$ | H | red |
| 10 | 4-Aminoazobenzene | —CH$_2$CH$_3$ | —Cl | H | scarlet |
| 11 | 4-Aminoazobenzene | —CH$_2$CH$_3$ | —NHCOCH$_3$ | H | maroon |
| 12 | 4-Aminoazobenzene | —CH$_2$CH$_3$ | —CH$_3$ | —OCH$_3$ | maroon |
| 13 | 4-Aminoazobenzene | —CH$_2$CH$_3$ | —OCH$_3$ | —OCH$_3$ | maroon |

EXAMPLE 14

2-Methoxy-4-nitro-5-methylaniline (9.1 parts) was pasted in 50 parts of water and 15 parts of concentrated hydrochloric acid and diazotized at 15°–20° C. by addition of a solution of 3.7 parts of sodium nitrite.

tate, then iced to 0°. The products precipitated rapidly and were filtered, after raising the pH to 9.5 and dried. All were dark colored solids having somewhat limited solubility in water, but dyeing nylon from alkaline baths in the shades listed.

TABLE II

| Example No. | Coupler Used | Shade of Dyeing On Nylon |
|---|---|---|
| 16 | N-Methyl-N-phenyl-3-amino-propane sulfonic acid | Navy |
| 17 | N-Cyclohexyl-N-phenyl-3-amino-propane sulfonic acid | Navy |
| 18 | N-Benzyl-N-phenyl-3-amino-propane sulfonic acid | Reddish-navy |
| 19 | N-(2-Hydroxyethyl)-N-phenyl-3-amino-propane sulfonic acid | Navy |
| 20 | N-Ethyl-N-(m-tolyl)-3-amino-propane sulfonic acid | Greenish-navy |
| 21 | N-Ethyl-N-(1-naphthyl)-3-amino-propane sulfonic acid | Reddish-navy |
| 22 | N-Ethyl-N-(2,5-dimethoxyphenyl)-3-amino-propane sulfonic acid | Green-grey |
| 23 | N-Ethyl-N-(m-chlorophenyl)-3-aminopropane-sulfonic acid | Reddish-navy |

I claim:

1. A water-soluble compound having the structure:

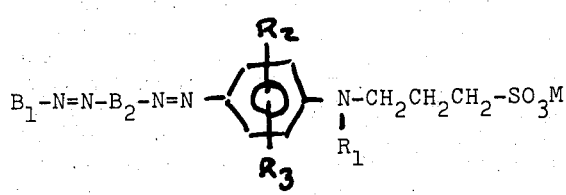

wherein $R_1$ is alkyl having 1–8 carbon atoms, benzylcyclohexyl, —$CH_2CH_2OH$, $$-CH-CH_2CH_2OH,$$
$$\ \ |$$
$$CH_3$$

$$-CH_2-CH-CH_2OH-CH_2CH_2CN,$$
$$\ \ \ \ \ \ \ \ \ |$$
$$\ \ \ \ \ \ \ \ CH_3$$

—$CH_2CH_2$—O—$COCH_3$ or $$-CHCH_2-O-COCH_3;$$
$$\ \ |$$
$$CH_3$$

$R_2$ is —H, -alkyl having 1 to 4 carbon atoms, halogen, —O—alkyl having 1 to 4 carbon atoms or —NH—$COR_4$;

$R_3$ is —H, —alkyl having 1 to 4 carbon atoms, —O—alkyl having 1 to 4 carbon atoms or —NH—$COR_4$;

$R_4$, as used in $R_2$, $R_3$, $R_5$ and $R_6$, represents -alkyl having 1 to 4 carbon atoms, -tolyl, -phenyl or -halophenyl;

$B_1$ is phenyl or phenyl substituted with nitro, halogen, cyano, lower alkyl, lower alkoxy, trifluoromethyl, alkylsulfonyl, acetyl, carboxamido, sulfonamido, N-alkyl-sulfonamido, N,N-dialkylsulfonamido, N-alkylcarboxamido and carboxyl;

$B_2$ is 1,4-naphthylene or

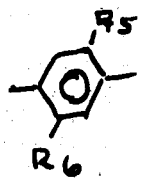

$R_5$ is —H, -alkyl, -alkoxy, or —$NHCOR_4$;
$R_6$ is —H, -alkyl, -alkoxy, —$NHCOR_4$, —NH—$SO_2$—$R_4$ or halogen; and
M represents —H, —Na, —K, —Li or —N—$NH_4$.

2. A compound according to claim 1 having the structure:

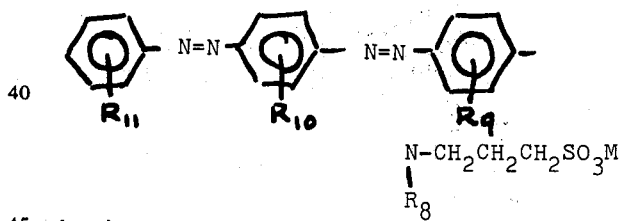

wherein $R_8$ is -alkyl having 1 to 8 carbons, —$CH_2CH_2CN$, -cyclohexyl, or -benzyl;
$R_9$ is —H or —$CH_3$;
$R_{10}$ is H or —$CH_3$; and
$R_{11}$ is H or $CH_3$ 3. A compound according to claim 1 having the structure:

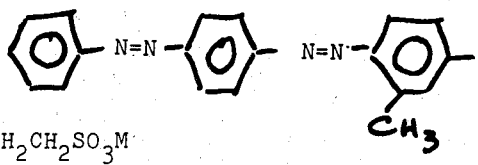

* * * * *

UNITED STATES PATENT OFFICE
CERTIFICATE OF CORRECTION

PATENT NO. : 3,971,769
DATED : July 27th, 1976
INVENTOR(S) : James F. Feeman

It is certified that error appears in the above-identified patent and that said Letters Patent are hereby corrected as shown below:

In the masthead, at [63]:

"Jan. 17," should read --Jan. 19,--

Column 1, Line 4:

"Jan. 17," should read --Jan. 19,--

Signed and Sealed this

Nineteenth Day of October 1976

[SEAL]

Attest:

RUTH C. MASON
*Attesting Officer*

C. MARSHALL DANN
*Commissioner of Patents and Trademarks*